(12) United States Patent
Knezevic et al.

(10) Patent No.: US 8,779,312 B2
(45) Date of Patent: Jul. 15, 2014

(54) METHOD AND DEVICE FOR ANALYZING BIOMOLECULES WITH TRACK-ETCHED POLYMERIC LAYERS

(75) Inventors: Vladimir Knezevic, Gaithersburg, MD (US); Dan-Paul Hartmann, Bethesda, MD (US); Michael R. Emmert-Buck, Easton, MD (US)

(73) Assignees: United States of America/NIH, Washington, DC (US); 20/20 Genesystems, Inc., Rockville, MD (US)

( * ) Notice: Subject to any disclaimer, the term of this patent is extended or adjusted under 35 U.S.C. 154(b) by 250 days.

(21) Appl. No.: 12/626,405

(22) Filed: Nov. 25, 2009

(65) Prior Publication Data
US 2010/0137160 A1 Jun. 3, 2010

Related U.S. Application Data

(60) Division of application No. 11/277,227, filed on Mar. 22, 2006, now Pat. No. 7,838,222, which is a continuation-in-part of application No. 10/522,663, filed as application No. PCT/US03/24225 on Aug. 1, 2003, now abandoned, said application No. 11/277,227 is a continuation-in-part of application No. 10/627,352, filed on Jul. 25, 2003, now abandoned, which is a continuation of application No. 09/718,990, filed on Nov. 20, 2000, now Pat. No. 6,602,661, which is a continuation-in-part of application No. PCT/US00/20354, filed on Jul. 26, 2000, said application No. 11/277,227 is a continuation-in-part of application No. 10/048,194, filed as application No. PCT/US00/20354 on Jul. 26, 2000, now Pat. No. 7,214,477.

(60) Provisional application No. 60/400,874, filed on Aug. 2, 2002, provisional application No. 60/145,613, filed on Jul. 26, 1999.

(51) Int. Cl.
*H01H 1/40* (2006.01)
*C12Q 1/68* (2006.01)

(52) U.S. Cl.
USPC .......................... 200/506; 435/6.1

(58) Field of Classification Search
None
See application file for complete search history.

(56) References Cited

U.S. PATENT DOCUMENTS

| | | |
|---|---|---|
| 3,620,947 A | 11/1971 | Allen et al. |
| 4,176,069 A | 11/1979 | Metz et al. |
| 4,337,131 A | 6/1982 | Vesterberg |
| 4,613,567 A | 9/1986 | Yasoshima et al. |
| 4,716,101 A | 12/1987 | Thompson et al. |
| 4,795,562 A | 1/1989 | Walsh |
| 4,840,714 A | 6/1989 | Littlehales |
| 4,874,691 A | 10/1989 | Chandler |
| 5,047,135 A | 9/1991 | Nieman |
| 5,057,438 A | 10/1991 | Imai et al. |
| 5,078,853 A | 1/1992 | Manning et al. |
| 5,155,049 A | 10/1992 | Kauvar et al. |
| 5,173,159 A | 12/1992 | Dutertre |
| 5,238,651 A | 8/1993 | Chuba |
| 5,332,484 A | 7/1994 | Hilt |
| 5,387,325 A | 2/1995 | Opplt |
| 5,427,664 A | 6/1995 | Stoev et al. |
| 5,438,128 A | 8/1995 | Nieuwkerk et al. |
| 5,486,452 A | 1/1996 | Gordon et al. |
| 5,650,055 A | 7/1997 | Margolis |
| 5,679,310 A | 10/1997 | Manns |
| 5,716,508 A | 2/1998 | Starr |
| 5,741,639 A | 4/1998 | Ensing et al. |
| 5,827,749 A * | 10/1998 | Akers, Jr. ............. 436/534 |
| 5,843,657 A | 12/1998 | Liotta et al. |
| 5,968,745 A | 10/1999 | Thorp et al. |
| 5,993,627 A | 11/1999 | Anderson et al. |
| 6,013,165 A | 1/2000 | Wiktorowicz et al. |
| 6,064,754 A | 5/2000 | Parekh et al. |
| 6,087,134 A | 7/2000 | Saunders |
| 6,135,942 A | 10/2000 | Leptin |
| 6,232,067 B1 | 5/2001 | Hunkapiller et al. |
| 6,602,661 B1 | 8/2003 | Knezevic |
| 2002/0012920 A1 | 1/2002 | Gardner et al. |

FOREIGN PATENT DOCUMENTS

| | | |
|---|---|---|
| EP | 139373 | 5/1985 |
| EP | 0525723 | 2/1993 |
| WO | 98/20353 | 5/1998 |
| WO | 98/41863 | 9/1998 |
| WO | 00/67647 | 12/1999 |
| WO | 00/45168 | 8/2000 |
| WO | WO 02/48674 | * 6/2002 |

OTHER PUBLICATIONS

"General Specifications for SPI-Pore TM Polycarbonate Track Etch Membrane Filters", (web page http://www.2sp.com/catalog/spec_prep/spi-pore.html, date 1999).*

Cleeve & Tua, "Isoelectric focusing of human tissue alkaline phosphatase isoenzymes in agarose gell," Clinica Chimica Acta 137:333-340, 1984.

Demczuk et al., "Identification and analysis of all components of a gel retardation assay by combination with immunoblotting," Proc. Natl. Acad. Sci. USA 90:2574-2578, Apr. 1993.

Englert et al., "Molectular profiling of human cancer: new opportunities," Curr. Opin. Mol. Therap. 1(6): 712-719, 1999.

(Continued)

*Primary Examiner* — Nancy T Vogel
(74) *Attorney, Agent, or Firm* — Whiteford, Taylor & Preston, LLP; Joseph L. Morales

(57) ABSTRACT

The present disclosure provides methods, devices and kits that permit large numbers of target biomolecules to be detected simultaneously in samples originating from a multi-sample holder, such as a multi-well plate. One specific example method is a method of making multiple substantial replicas of a biomolecular content of a multi-well sample holder. Devices and kits for carrying out the described methods are also provided.

6 Claims, 7 Drawing Sheets

(56) References Cited

OTHER PUBLICATIONS

Englert et al., "Layered Expression Scanning: Rapid Molecular Profiling of Tumor Samples," Cancer Res. 60:1526-1530, Mar. 15, 2000.
Huekeshoven & Dernick, "Effective blotting of ultrathin polyacrylamide gels anchored to a solid matrix," Electrophoresis 16:748-756 1995.
Inczedy-Marcsek et al., Extraction of Proteins . . . of Cryostat sections and tissue culture specimens, Acta Histochemica, Suppl.—Band XXXVI S:377-394, 1988.
Legocki et al., "Multiple Immunoreplica . . . One Polyacrylamide Gell," Anal. Biochem. 111:385-392, 1981.
Manabe et al., "An Electroblotting Apparatus . . . Two-Dimensional Gels," Anal Biochem. 143:39-45, 1984.
Neumann et al., "Replica blotting . . . two-dimensional elecrophoresis," Electrophoresis 19:752-757, 1988.
Olsen et al., "Diffusion blotting for . . . on a solid support," J. Immunol. Methods 220:77-84, 1988.
Sanchez et al., "Simultaneous analysis of cyclin . . . monoclonal antibody immunoblots," Electrophoresis 18:638-641, 1997.
Schumacher et al., "Direct Tissue Isoelectric . . . Immunohistochemistry," Histochemical Journal 22:433-438, 1990.
Schumacher et al., "Direct Tissue Isoelectric . . . Characterization in Histochemistry," Anal. Biochem 194:256-258, 1991.
Van Der Sluis et al., "Immunochemical Detection . . . gel Isoelectric Focusing," Electrophoresis 9:654-661, 1988.
Braun et al., "Modified Diffusion Blotting . . . with PhastSystem," Electrophoresis 10:249-253, 1989.
Pappalardo, et al., "Microdissection, microchip arrays . . . (Primary and Metastases)," Seminars in Radiation Oncology 8(3): 217-223, 1988.
Schena et al., Science 270, 467-470, 1995.
Huang et al., Anal. Biochem. 268:305-317, 1999.
Hanot et al., "Expanding the use of track-etched membranes," Medical Devicelink Webpage, www.devicelink.com/grabber.php3?URL=http://www.devicelink.com/ivdt/archive/02.

* cited by examiner

US 8,779,312 B2

METHOD AND DEVICE FOR ANALYZING BIOMOLECULES WITH TRACK-ETCHED POLYMERIC LAYERS

REFERENCE TO RELATED APPLICATION(S)

This is divisional application of co-pending U.S. application Ser. No. 11/277,227, filed Mar. 22, 2006, which is a continuation-in-part of co-pending U.S. application Ser. No. 10/522,663, which is a 35 U.S.C. §371 U.S. national stage of PCT/US2003/024225, filed Aug. 1, 2003, which claims the benefit of U.S. provisional application No. 60/400,874, filed Aug. 2, 2002; and a continuation-in-part of co-pending U.S. application Ser. No. 10/627,352, filed Jul. 25, 2003, which is a continuation of U.S. application Ser. No. 09/718,990, filed Nov. 20, 2000 and now issued as U.S. Pat. No. 6,602,661, which in turn is a continuation-in-part of PCT/US00/20354, filed Jul. 26, 2000, which claims the benefit of U.S. provisional application No. 60/145,613 filed Jul. 26, 1999; and further is a continuation-in-part of co-pending U.S. application Ser. No. 10/048,194, which is a .sctn.371 U.S. national stage of PCT/US00/20354, filed Jul. 26, 2000, which also claims the benefit of U.S. provisional application No. 60/145,613, filed Jul. 26, 1999. Each of the applications from which priority and/or benefit is claimed is incorporated herein in its entirety.

STATEMENT OF GOVERNMENT RIGHTS

At least one of the inventors is an employee of an agency of the Government of the United States, and the Government may have certain rights in the subject matter claimed herein.

FIELD OF THE DISCLOSURE

The present disclosure is directed to methods of and devices and kits for, making multiple, substantially similar replicas of the biomolecular content in samples contained in a multi-sample holder, such as a multi-well plate. The disclosure further relates to using these methods, devices, and kits in determining the function and role of biomolecules (e.g., in disease), and to correlating the presence, absence, or quantity of one or a combination of biomolecules with a condition or state, such as particular diseases, prognoses, or responses to therapies.

BACKGROUND OF THE DISCLOSURE

An important approach to developing new drugs is high-throughput screening of compounds. Once a biological molecule is identified as a candidate target for therapeutic intervention thousand of compounds are developed and screened for their ability to interact (e.g. inhibit activity) with the biomolecules.

Many pharmaceutical companies have set minimum goals of screening 500,000 compounds per year against each of more than 100 targets. To reach this goal about 200,000 compounds must be screened every weekday of the year.

There are several screening processes that are utilized for candidate therapeutic agents, including measurement of the binding characteristics between the drug and the identified biomolecules and determination of the effects of the drug agent on biomolecule function. One of the most important screening processes is the use of in vitro cell lines as a bioassay system. This approach allows investigators to determine the effect of the therapeutic agent on the target biomolecule as it exists in a complex, living cellular milieu. The effect of the agent on biomolecule function can be determined, as well as other important parameters such as effective dose range of the agent, half-life of the drug, and ability of the agent to enter a living cell. Moreover, the efficacy and potential toxicity of the drug can be determined by monitoring changes in cellular viability, behavior and phenotype.

Candidate therapeutic agents are often screened in multi-well plates, such as 96- or 384-well plates. Various instrumentation including pipettes and robotic machinery have been designed to accommodate these formats. Multi-well test plates are well known in the art and are exemplified by those described in U.S. Pat. Nos. 4,304,865; 5,219,528; and 5,679,310.

With present techniques only one target may be identified in each well of a multi-well plate. However, many new targeted therapies and drug combinations have the effect of interacting with multiple proteins, for example, with proteins in signaling pathways. It would therefore be desirable to have a method and device for simultaneously surveying the effects of multiple drugs and/or candidate compounds on multiple targets in parallel. Furthermore, it would be desirable for such a method and device to be compatible with the instruments and procedures typically employed in high-throughput screening operations. It would also be desirable for such method and device to be employed for selecting drugs or drug combinations for particular patients based on the effects of the drugs on cellular material from the patient.

SUMMARY OF THE DISCLOSURE

The present disclosure provides methods, devices and kits that permit large numbers of target biomolecules to be detected simultaneously in samples originating from a multi-sample holder, such as a multi-well plate. The provided parallel systems enhance scientific accuracy by eliminating variability inherent in testing separate multi-well plates, and avoids much of the time and expense of preparing and screening multiple plates.

By way of example, described techniques permit candidate compounds applied or administered to samples in a multi-well plate to be screened for activity against multiple biomolecules in a parallel, high-throughput manner.

According to one method of the present disclosure, biomolecules from a plurality of wells of a multi-well plate are simultaneously transferred from the plate wells onto a plurality of membranes. Each membrane has a high affinity, but a low capacity, for the biomolecules. This allows the creation of multiple substantial replicas or imprints or "copies" of a biomolecular content of the plate of samples (in that a portion of one or more, or all, of the biomolecules in each loaded well of the plate is captured, directly or indirectly, by membranes in the stack). The membranes are then separated can then be subjected to subsequent analysis.

For instance, in some examples membranes from the stack incubated with one or more detectors specific for a particular biomolecule or subset of biomolecules of interest. For example, the membranes may be incubated with different antibodies or cocktails of antibodies, ligands, receptors, etc. In certain embodiments (e.g., where membranes in the stack are similar to each other), each membrane has substantially the same pattern of biomolecules bound to it; therefore, different biomolecules can be detected on each membrane by applying different detector(s) to each membrane.

In some embodiments, affinity or "bioaffinity" membranes are employed, where two or more membranes in the stack are pre-treated with an affinity enhancing molecule (e.g., antibodies, nucleic acid or other probes, or other capture molecules) or a series of different affinity enhancing molecules (e.g., a different one on each membrane). The affinity enhancing molecule(s) are bound directly to the membranes so that each layer captures a different target biomolecule of interest.

The present disclosure is also directed to kits, including kits that comprise a set of two or more membranes for use in one of the described methods. In one embodiment, a kit includes a set of membranes and, optionally, separate vials of two or more detectors, such as an antibody, related detection chemistries, transfer buffer, instructions and/or labels that indicate the particular detector to be applied to particular membrane. Software useful for analyzing the membranes may also be included in the kit, or in some embodiments will be accessible via modem or the Internet.

The foregoing and other features and advantages will become more apparent from the following detailed description of several embodiments, which proceeds with reference to the accompanying figures.

DETAILED DESCRIPTION

I. Description of Several Embodiments

Figure 1:
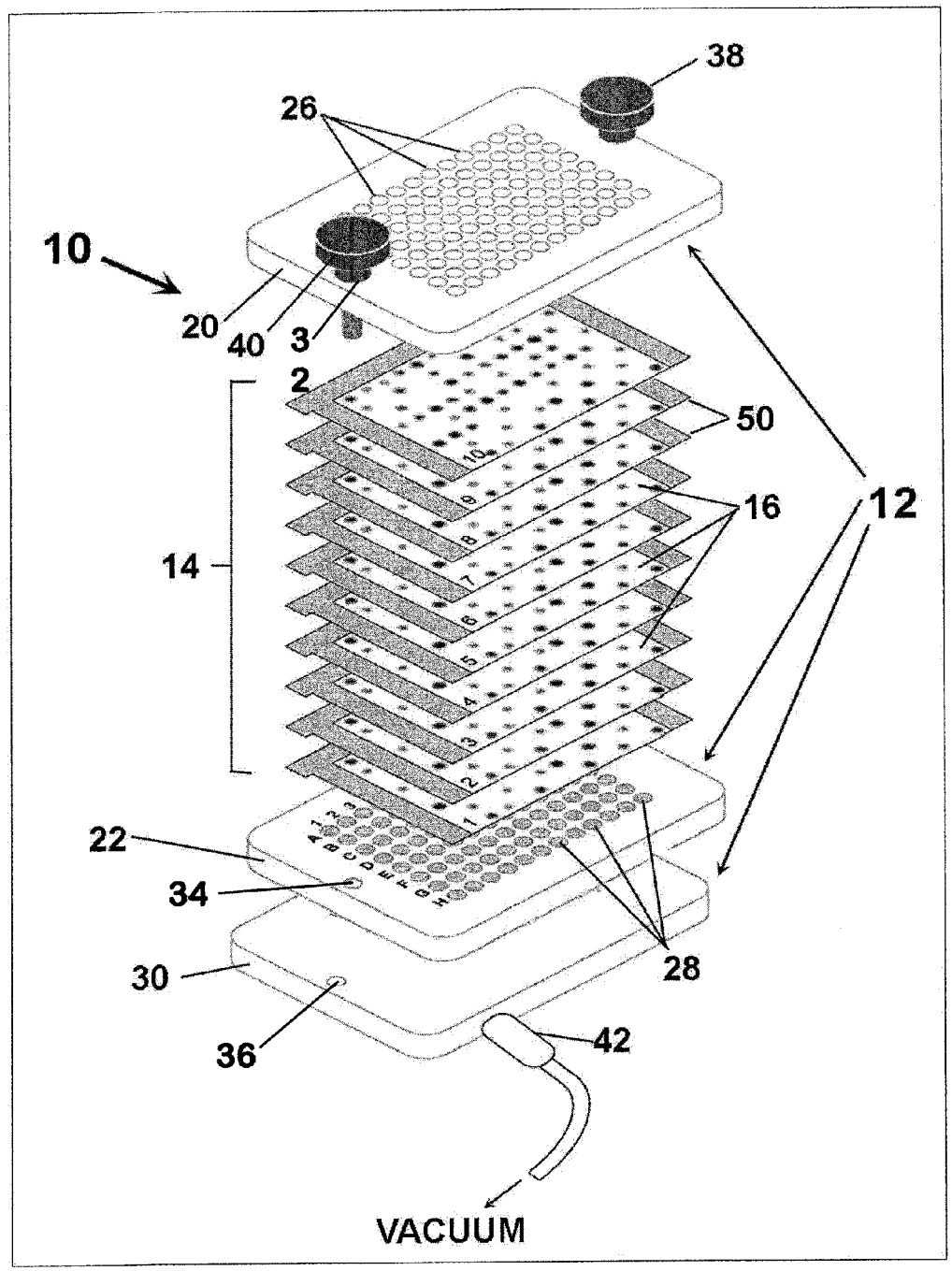
FIG. 1 is an exploded perspective view of one embodiment of a membrane stack and blotting apparatus, as described herein.

A first embodiment is a method of making multiple substantial replicas of a biomolecular content of a multi-well sample holder. In examples of this embodiment, the method involves providing a multi-well sample holder in physical contact with a stack of membranes (e.g., 5 or more membranes); applying two or more samples comprising biomolecules to at least two wells of the multi-well sample holder, under conditions that (a) allow at least a portion of the samples to pass through the stack of membranes; and (b) allow the multiple membranes to capture at least a portion of the biomolecules from each of the samples, thereby forming multiple substantial replicas of the biomolecular content of the multi-well sample holder. By way of example, the biomolecules comprise proteins, nucleic acids (for instance, DNA, RNA, or mixtures thereof), or mixtures thereof.

In some embodiments, each of the membranes comprises a porous substrate having a thickness of less than 30 microns and no less than 4 microns. By way of example, the porous substrate may include polycarbonate, cellulose acetate, and mixtures thereof.

In some embodiments, one or more of the membranes comprise a material for increasing an affinity of at least one of the membranes to the biomolecules. For instance, the material is coated on one or more of the membranes. In specific examples, the material for increasing affinity is selected from the group consisting of nitrocellulose, poly-L-lysine, and mixtures thereof.

In other examples of methods of making multiple substantial replicas of a biomolecular content of a multi-well sample holder, the conditions that allow at least a portion of the samples to pass through the multiple membranes involve applying at least partial vacuum that encourages movement of the sample through the stack of membranes in a desired direction of movement. In other examples, the conditions that allow at least a portion of the samples to pass through the multiple membranes involve providing a wick that facilitates movement of the sample through the stack of membranes in a desired direction of movement.

Other provided methods further involve correlating the biomolecules transferred to and/or detected on the one or more membranes with a biological characteristic of the sample(s).

Another example method is a method of detecting one or more biomolecules, which method further involves detecting at least one biomolecule of interest on at least one of the multiple membranes. By way of example, detecting biomolecules of interest comprises exposing at least one of the multiple membranes to a detector. In other examples, detecting the biomolecules involves separating one or more of the membranes from the stack, and detecting the biomolecules on one or more of the separated membranes. For instance, the multiple membranes are separated from each other and from the remainder of the sample prior to detecting the biomolecules of interest.

Yet another embodiment is a method for identifying one or more biomolecules from a plurality of wells in a multi-well plate, which method involves providing a multi-well plate assembly; providing a stack of at least two membranes; operatively securing the stack to the multi-well plate assembly; introducing biomolecules into two or more wells of the multi-well plate; transferring biomolecules from the wells to multiple membranes in the stack; separating the membranes; and identifying the one or more biomolecules on the multiple membranes. By way of example, biomolecules useful in such methods include proteins, nucleic acids (e.g., DNA molecules, RNA molecules, and so forth) or mixtures of two or more thereof.

II. Abbreviations and Terms

BSA bovine serum albumin
cDNA complementary deoxyribonucleic acid
DMEM Dulbecco's modified Eagle's medium
DPBS Dulbecco's phosphate-buffered saline
FBS Fetal bovine serum
TRIS tris(hydroxymethyl)aminomethane\

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments disclosed herein, the following explanations of specific terms are provided:

"Addressable" refers to that which is capable of being reliably and consistently located and identified, as in an addressable location on an array, such as a multi-well plate.

"Affinity" means the chemical attraction or force between molecules.

"Amplification," when used in reference to nucleic acid samples, means any one of a variety of techniques that increase the number of copies of a nucleic acid molecule in a sample or specimen. An example of amplification is the polymerase chain reaction. Other examples of amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134). Amplification of nucleic acids is easily and routinely carried out on samples in multi-well plates.

"Antibody cocktails" means mixtures of between two to about 100 different detector antibodies.

"Apparatus" or "device" means a mechanical object or set of objects designed or provided for a particular use. The terms "apparatus" and "device" are used synonymously herein.

"Array" means two or more.

"Biological sample" means any material containing biomolecules, whether solid, liquid or gas, including but not limited to, e.g., organs, tissues, bodily fluids, hairs, cells in suspension or pelleted, cell or tissue extracts, and gels or other materials used to separate and/or immobilize biomolecules (e.g., agarose gels and polyacrylamide gels), as well as materials in containers of biomolecules such as microtiter plates.

"Biomolecular content," when used in the context of a multi-sample holder (or plate) such as a multi-well plate, encompasses the totality of the biomolecules contained in one, more than one, or all samples present on the plate, wherein the biomolecules contained in each sample on the plate maintain the same relative two-dimensional relationships (relative to the plane of the membrane(s) in the plate) to the biomolecules contained in every another sample in the plate. For example, the biomolecular content of a three-well sample holder having Well 1, Well 2 and Well 3 arranged in a single, straight row, in that order, with wells 1, 2, and 3 containing samples of biomolecules A, B, and C, respectively, is "A B C" in that order.

When used in the context of a single sample, the term "biomolecular content" means the type(s) and/or amount(s) of biomolecule(s) contained in that particular sample.

"Biomolecules" are molecules of biological origin, which are typically produced by, obtained from, excreted by, secreted by or derived from living organisms (including microorganisms, viruses, plants, animals, and humans), or a degradation product of such a molecule. The term biomolecules includes, without limitation, peptides, proteins, glycoproteins, nucleic acids, fatty acids, and carbohydrates.

"Capacity" means the ability to receive, hold, adsorb or absorb molecules (such as biomolecules) from a sample.

"Captor" means a molecule, such as an antibody or nucleic acid (e.g., DNA) probe, that is anchored to a surface (such as a membrane) and has an affinity (such as a specific affinity) for a target biomolecule.

"Capture" means to bind, whether by specific or non-specific or direct or indirect interaction. For example, a membrane may capture a biomolecule by virtue of a non-specific interaction, such as electrostatic forces, formed between the membrane surface and all or part of the biomolecule (also called "direct capture," see below). In another example, a membrane may capture a biomolecule by virtue of a captor molecule that is anchored to the membrane (also called "indirect capture," see below).

"cDNA" refers to a DNA molecule lacking internal, non-coding segments (introns) and regulatory sequences which determine transcription. cDNA may be synthesized in the laboratory by reverse transcription from messenger RNA extracted from cells.

"Counter-ligand staining" is intended to refer to any detection technique that detects the presence of ligand that is not bound to a protein of the biological sample, and thus reveals (as, for example, by an absence of staining, etc.) the presence of ligand that is bound to a protein of the biological sample.

"Detector" means a molecule, such as an antibody or DNA probe, that is free in solution (i.e., not anchored to a membrane) and has an affinity for one of the sample components.

"Direct capture" means the conjugation or binding of a biomolecule directly onto a surface (such as the surface of a membrane) without the aid of a captor.

"DNA" is a long chain polymer that contains the genetic material of most living organisms (the genes of some viruses are made of ribonucleic acid (RNA)). The repeating units in DNA polymers are four different nucleotides, each of which includes one of the four bases (adenine, guanine, cytosine, and thymine) bound to a deoxyribose sugar to which a phosphate group is attached. Triplets of nucleotides (referred to as codons) code for each amino acid in a polypeptide, or for a stop signal. The teem "codon" is also used for the corresponding (and complementary) sequences of three nucleotides in the mRNA into which the DNA sequence is transcribed.

"Fluorophore" refers to a chemical compound, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515-540λ. Red fluorophores, for example Texas Red, Cy5 and tetramethylrhodamine, are characterized by their emission at wavelengths generally in the range of 590-690λ.

Examples of fluorophores that may be used are provided in U.S. Pat. No. 5,866,366 to Nazarenko et al., and include for instance: 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl) phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]

naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include GFP (green fluorescent protein), Lissamine™, diethylaminocoumarin, fluorescein chlorotriazinyl, naphthofluorescein, 4,7-dichlororhodamine and xanthene and derivatives thereof. Other fluorophores known to those skilled in the art may also be used.

"High throughput screening" refers to techniques for analysis of large numbers of samples (e.g., more than 50, for instance, 96 or more, such as 200, 500, 1000, 10,000, 20,000, 100,000, 500,000, or 1,000,000 or more samples) substantially in parallel. In certain examples, high throughput screens work with samples in multi-compartment sample holders (e.g., microtiter or other multi-well plates) to rapidly identify and/or test large numbers of compounds, nucleic acids, proteins and/or other biomolecules, for example, to determine the structure, expression, or function of each of such biomolecules, or, for example, to distinguish the structure, expression, or function of such compounds, nucleic acids, proteins or other biomolecules in normal as compared to abnormal cells or tissues.

"Hybridization" refers to an interaction between nucleic acid molecules that are complementary to each other. Hybridization is based on hydrogen bonding, which includes Watson-Crick, Hoogsteen, or reversed Hoogsteen hydrogen bonding between complementary nucleotide units. For example, adenine and thymine are complementary nucleobases that pair through formation of hydrogen bonds. "Complementary" refers to sequence complementarity between two nucleotide units. For example, if a nucleotide unit at a certain position of an oligonucleotide is capable of hydrogen bonding with a nucleotide unit at a certain position of a DNA or RNA molecule, then the nucleotides at those positions are complementary to each other. The oligonucleotide and the DNA or RNA are complementary to each other when a sufficient number of corresponding positions in each molecule are occupied by nucleotide units which can hydrogen bond with each other. "Specifically hybridizable" and "complementary" are terms that indicate a sufficient degree of complementarity such that stable and specific binding occurs between the oligonucleotide and the DNA or RNA target. An oligonucleotide need not be 100% complementary to its target DNA sequence to be specifically hybridizable.

Hybridization conditions resulting in particular degrees of stringency will vary depending upon the nature of the hybridization method of choice and the composition and length of the hybridizing DNA used. Generally, the temperature of hybridization and the ionic strength (especially the Na+ concentration) of the hybridization buffer will determine the stringency of hybridization. Calculations regarding hybridization conditions required for attaining particular degrees of stringency are discussed by Sambrook et al. *Molecular Cloning: A Laboratory Manual*, Cold Spring Harbor Laboratory Press (1989), chapters 9 and 11, herein incorporated by reference "Indirect capture" means the conjugation or binding of a target biomolecule onto a captor, which in turn is bound to a surface, such as the surface of a membrane. Thus, with indirect capture the target biomolecule is not directly conjugated to the membrane.

"Label" refers to detectable markers or reporter molecules, which can be attached for instance to a specific biomolecule (e.g., a nucleic acid, protein, lipid). Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

"Membrane" means a thin sheet of natural or synthetic material that is porous or otherwise at least partially permeable to fluid and/or biomolecules.

"Microarray" is an array comprising addressable locations (which for instance are occupied by one or more molecule, such as isolated biomolecules or mixtures of biomolecules) that is miniaturized so as to require microscopic examination for (e.g., visual) evaluation. Usually the positions of features on an array or microarray are addressable, in that they can be located spatially within the two-dimensional space identified by the surface of the array itself.

"Multi-well sample holder" is any structure, usually a non-naturally occurring structure, capable of (i) holding at least two, biomolecule-containing samples in a defined two-dimensional relationship to each other within the plane defined by a surface of the holder, and (ii) being operatively secured to a stack of membranes, in such a way that samples can be transferred to and through the membranes. For example, a multi-well plate, such as a 6-well, a 36-well, a 96-well, or a 384-well plate, that permits samples to be applied to any or all of the wells of the plate, where such samples may then pass from the wells to and through a stack of membranes operably secured to the plate (e.g., at the bottom surface of the plate, when there is one or more opening in the bottom of each of the wells, so disposed to permit transfer of the sample to the membrane stack).

"Nucleic acid" refers to a deoxyribonucleotide or ribonucleotide polymer in either single or double stranded form, and unless otherwise limited, and encompasses known analogues of natural nucleotides that hybridize to nucleic acids in a manner similar to naturally occurring nucleotides.

"Operatively secured" means secured in a functional relationship, e.g., in direct or indirect physical contact. For example, a multi-well sample holder is operatively secured to a stack of membranes when samples in the multi-well sample holder may pass from the wells of the sample holder into the stack of membranes, whether passively or by an assisted mechanism, e.g., as a result of an applied vacuum, and biomolecules contained in the samples maintain the same relative spatial relationship that their respective samples had in the sample holder (e.g., in a two-dimensional array of wells).

"Polypeptide" means any chain of amino acids, regardless of length or post-translational modification (e.g., glycosylation or phosphorylation).

"Proteomics" means the identification or analysis of a proteome. A proteome is the group of proteins expressed and/or present in a biological sample.

"Stack" refers to a plurality (e.g., 2, 3, 4, 5, 8, 9, 10, 15, 20, 50, 100 or more) of adjacent substrates, whether oriented horizontally, vertically, at an angle, or in some other direction. The substrates (e.g., membranes) may be spaced or touching, for example contiguous. More generally, membranes in a stack may be referred to as layers (within a stack).

"Subject" refers to living, multicellular vertebrate organisms, a category that includes both human and veterinary subjects for example, mammals, birds, and particularly primates.

"Substantial replicas," as used herein, are membranes whereupon biomolecules from samples originally contained in a multi-well sample holder are captured in positions that correspond to the original positions (in the two dimensions defined by the face of the multi-well sample holder or the surface of the stack to which the sample holder was applied) of the samples in the multi-well sample holder. It is understood, however, that the maintenance of position is relative rather than absolute, and the replicates produced by methods described herein are not limited to exact identical copies of the two-dimensional architecture of the starting collection of samples.

"Two-dimensional relationship" or "relative relationship" refers to the physical location of two objects in relation to each other in two dimensions of space. The two dimensions are usually defined by some surface of reference, for instance one surface of a three-dimensional object such as a multi-well sample holder, or a surface of a substantially two-dimensional object such as a membrane (which has a negligible third-dimension, thickness, compared to its width and length). For instance, samples in two or more wells of a multi-well sample holder are in a defined two dimensional relationship to each other, in that the two samples can be located and identified, relative to each other, in a two dimensional space that is defined by the face of the multi-well sample holder.

Samples applied to the wells of a multi-well sample holder may have the same composition of biomolecules or not. In various embodiments herein, a sample in one well contains nucleic acids and a sample in a second well contains proteins and a sample in third well contains a mixture of nucleic acids and proteins, and the three samples are in defined two-dimensional relationships to one another, for instance based on their positions within a microtiter plate (which is in and of itself a form of array), and so forth. Methods are provided wherein samples in a multi-well sample holder having a defined two-dimensional architecture (wherein the samples are maintained in defined two-dimensional relationships relative to each other) are transferred from the sample to membranes of a stacked array of membranes. Particularly, in such methods the two-dimensional architecture is substantially maintained during the transfer. Thus, biomolecules contained in the sample that are captured on the membranes are captured in positions that correspond to the positions (in the two dimensions defined by the face of the sample and the surface of the membrane stack to which the sample was applied) they held relative to each other in the starting samples. It is understood, however, that the maintenance of position is relative rather than absolute, and the replicates produced by methods described herein are not limited to exact identical copies of the two-dimensional architecture of the starting sample.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Apparatus for Making Multiple Substantial Replicates of Samples in a Multi-Well Sample Holder Methods and devices for identifying multiple biomolecules in samples, in particular samples in multi-well plates, are disclosed herein. As illustrated in FIG. 1, in a first embodiment apparatus 10 generally comprises a plate assembly 12 to which membrane stack 14 is disposed. The sample contents of the wells (e.g. cell lysates) are made to pass through membrane stack 14, whereupon biomolecules (for instance, proteins and nucleic acids) are captured on each of the layers 16 of the stack of membranes. Layers 16 can then be separated and particular biomolecules can be detected on each layer using conventional techniques, such as for instance immunoblotting for protein, hybridization for nucleic acids, and so forth.

Plate Assembly

Figure 2:
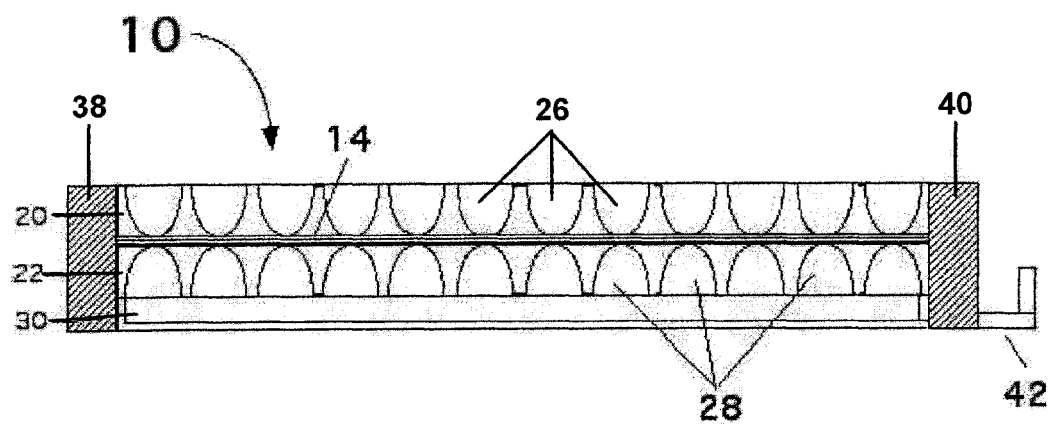
FIG. 2 is a side section view of a membrane stack and blotting apparatus according to one embodiment disclosed herein.

With reference to FIGS. 1 and 2, plate assembly 12 according to a first embodiment comprises upper plate 20 and lower plate 22 each defining a plurality of axially aligned wells 26 and 28. A vacuum chamber 30 is provided adjacent to lower plate 22 and is adapted to draw fluids through the apparatus. Membrane stack 14 comprising a plurality of membranes 16 is sandwiched between upper plate 20 and lower plate 22 for capturing proteins and other biomolecules drawn through the apparatus. Each of upper plate 20, lower plate 22, and vacuum chamber 30 define apertures 32, 34 and 36 adapted to be axially aligned and to receive bolts 38 and 40. Tightening bolts 38 and 40 permits stack 14 to be compressed between upper plate 20 and lower plate 22, as shown in FIG. 2.

A variety of commercially available dot and slot blotting manifolds may be used for plate assembly 12 including the Hybri-Dot 96-Well Filtration Manifold available from Invitrogen (Carlsbad, Calif.) and related dot and slot blotters from Topac (Highland, Mass.) and MBI Fermentas (Hanover, Md.). The number of wells in the manifold selected will vary depending on the needs of the user and the instrumentation with which apparatus 10 will be used. Typical formats include 24, 96, 384 and 1536 wells. Such formats are compatible with multi-channel pipettors and robotic instruments used in high-throughput screening operations. Upper plate 20, lower plate 22, and vacuum chamber 30 may be machined from high-density acrylic or the like. Alternatively, lower plate 22 and vacuum chamber 30 can be combined into a unitary structure which includes a sealing member for engagement with the lowest-most membrane 16. Such a unitary unit is commercially available from Bio-Rad Corp. (Hercules, Calif.) under the name Bio Dot Microfiltration System. Importantly, the material employed must give sufficient rigidity to the plates so that pressure can be applied to both sides of membrane stack 14. As best viewed in FIG. 2, wells 26 and 28 preferably have an "hour glass" configuration to permit sample delivery onto the membranes in a concentrated manner.

A coupling 42 is mounted to an aperture defined in a wall of vacuum chamber 30. A tube connected to a vacuum (not shown) of the type conventionally used in laboratories may be attached to coupling 42 to create the vacuum for pulling the sample through membrane stack 14.

Membranes and Frames

As best viewed in FIG. 1 membrane stack 14 comprises a plurality of membranes 16 positioned in a layered configuration. The dimensions of membranes 16 generally corresponding to the dimensions of the multi-well plate to which it is to be applied, e.g., about 12.4 cm by about 16 cm. Depending on the nature of the manifold employed it may be desirable to have the membranes extend beyond the periphery of the manifold to perfect an air-tight seal. Alternatively, a groove, which is shaped to receive the membranes, may be defined in either or both of upper plate 20 and/or lower plate 22.

The number of membranes 16 included in stack 14 can vary significantly depending on the number of proteins to be detected from the plate. For most applications, about 5 to 25 membranes will be sufficient. The stacks of membranes are commercially available from 20/20 GeneSystems, Inc. (Rockville, Md.). The stack is oriented so that each membrane 16 can make direct contact with the adjacent membranes during the transfer process.

Membranes 16 may be constructed in the manner disclosed in PCT International Application Nos. PCT/US03/02933, filed Jan. 31, 2003, and PCT/US01/44009, filed Nov. 20, 2001, each of which is incorporated herein in its entirety. In short, membranes 16 are constructed of a thin porous substrate that is coated with a material to increase the affinity of the membrane to the biomolecules being transferred thereto. The substrate is preferably constructed of polycarbonate or a similar polymeric material that maintains sufficient structural integrity despite being made porous and very thin. Instead of polycarbonate the substrate may be constructed of polyester, polyethylene phthalate, or of cellulose derivatives such as cellulose acetate, as well as polyolefins, (e.g. polyethlylene, polypropylene, etc.), gels, or other porous materials.

It is a particular feature of the certain embodiments that membranes 16 have a high affinity for biomolecules, such as proteins and nucleic acids, but have a low capacity for retaining such molecules. This feature permits the molecules to pass through the membrane stack with only a limited number being trapped on each of the layers thereby allowing multiple blots or substantial replicates to be generated. In other words, the low capacity allows the creation of multiple substantial replicates because only a limited quantity of biomolecules is trapped on each layer. More specifically, the affinity and capacity of membrane 16 should be such that, when at least 3 and preferably more than 10 membranes are stacked and exposed to a sample according to the methods disclosed herein, biomolecules of interest can be detected on any and all of the membranes including those positioned furthest from the sample.

To help ensure that the binding capacity of membrane 16 is sufficiently low to prevent the trapping of too many biomolecules in a sample, the thickness of the membrane should be less than about 30 microns, preferably between about 4 to about 20 microns and most preferably between about 8 to about 10 microns. The pore size of the substrate should preferably be between about 0.1 to about 5.0 microns, most preferably about 0.4 microns. Another advantage of using a thin membrane is that is lessens the phenomenon of lateral diffusion. The thicker the overall stack, the wider the diffusion of biomolecules moving through the stack. A thicker membrane could be employed with binding sites blocked to reduce its biomolecule-binding capacity.

The membrane substrate preferably includes a coating on one or both surfaces to increase its ability to bind proteins or other biomolecules. The coating is preferably nitrocellulose but other materials such as poly-L-lysine may also be employed. Before being applied to a membrane, the nitrocellulose is dissolved in methanol or other appropriate solvent(s) in concentration from about 0.1% to about 1.0%. In lieu of coating, nitrocellulose, or other materials with an affinity for proteins, can be mixed with the polycarbonate before the substrate is formed thereby providing an uncoated substrate having all of the desired characteristics of the membrane. Dip coating is preferred although alternative coating methods known in the art may be used in lieu of dip coating, including lamination and spraying. In all instances it should be understood that only one surface (i.e., the surface that faces the sample) need be coated instead of both.

The substrates are preferably "track-etched membranes" (a/k/a "screen membranes"), which are formed by a process that creates well-defined pores by exposing a dense film to ionizing radiation forming damage tracks. This is followed by etching of the damaged tracks into pores by a strong alkaline solution. A description of this process may be found on the Internet site of G. E. Osmonics (Minnetonka, Minn.) under the heading "Basic Principles of Microfiltration." Examples of membranes that may be employed as the substrate include the Isopore™ (polycarbonate film) membrane available from Millipore (Bedford, Mass.), the Poretics® Polycarbonate or Polyester membranes available from Osmonics (Minnetonka, Minn.) or the Cyclopore™ Polycarbonate or Polyester membranes available from Whatman (Clifton, N.J.).

To increase the surface area of the aforementioned track-etched membranes, which have a very smooth, flat surface, the coating might include a fiber or other material to give it a rougher texture. Alternatively, the surface area could be scratched or rubbed with an abrasive to increase the surface area available for binding.

In lieu of a track-etched membrane a tortuous pore membrane may be employed provided its capacity can be rendered low enough to permit a stack of three or more such membranes to be used according to the methods disclosed herein. This could be accomplished, for example, by casting the membrane very thin, far thinner that the thickness of depth membranes conventionally employed (i.e., 150 µm). Alternatively, blocking certain binding sites could lower the capacity of conventional depth membranes.

In an alternative embodiment each membrane may be coated with an antibody or other capture molecule having an affinity to a particular target in the manner set forth in UPCT/US00/20354, which is incorporated herein in its entirety.

Figure 5:
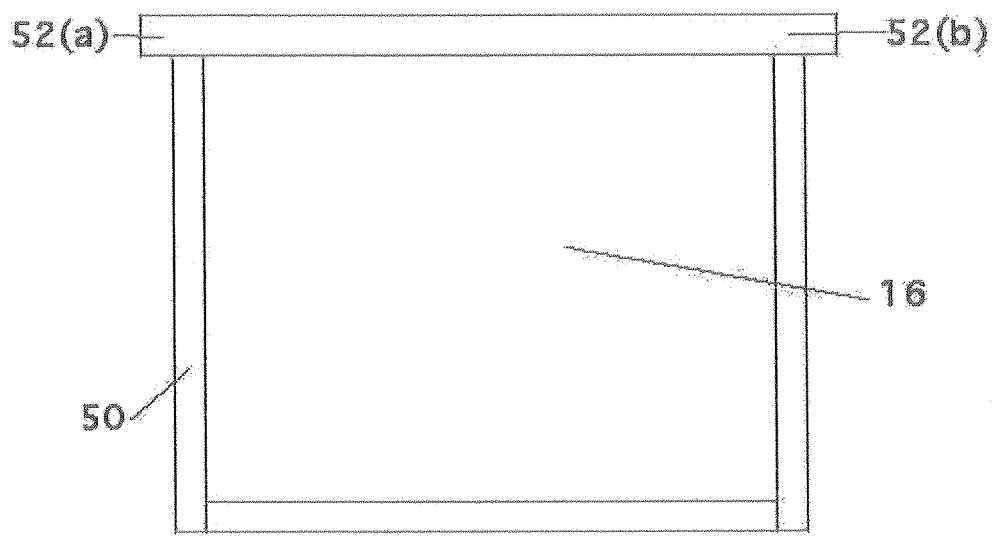
FIG. 5 is a front elevation view of a representative single membrane shown framed on all four sides.

In order to provide structural rigidity to membranes so that they may be separated from one another and individually processed, frames in some embodiments are mounted to the membranes. Frames may comprise a generally "U" shaped configuration covering three sides of the membranes while leaving one side open to permit the manual removal of air pockets in the manner described below. Alternatively, as shown in FIG. 5, frame 50 may cover all four sides of the membrane. The combination of the membranes and frames are referred to hereinafter as a "membrane unit."

The composition and dimensions of frames 50 is such that they provide sufficient structural rigidity for a user to grip the frame and manipulate the membranes as needed. At the same time, the frames should be sufficiently thin so that, when membrane units are stacked, the frames do not prevent protein transfer onto membrane stack 14. The width of frames 50 is preferably between about 0.3 to 0.7 mm and the thickness of the frames is between about 0.05 to 0.3 mm., most preferably about 0.1 mm thick. Thus, frame 50 is in some embodiments about ten times thicker than membrane 16.

In one embodiment, the materials that comprise frames 50 should be able to maintain their structure at temperatures of up to 80° C., but be able to melt when applied to a typical heat-sealing apparatus. One skilled in the relevant art will readily appreciate that a variety of compositions and configurations of frames 50 could meet these requirements. Examples of materials that may be employed to make frames 50 are transparency film (such as that available from Canon), or any thin plastic sheet made of polycarbonate, polyester or polyvinylchloride.

As readily viewed in FIG. 5, a pair of outwardly depending tabs 52 (a&b) are defined by frame 50. Each tab is adapted to be sealed to the corresponding tab on an adjacent membrane so as to hold stack 14 together during the transfer process. After biomolecules are transferred onto the membranes of stack 14, tabs 52 can be cut (e.g., with a scissors) so that the membranes may be separated and, for instance, incubated in separate detection solutions.

In the event there is leakage between frames 50, resulting in contamination of samples between layers, the use of membranes without frames ensures good tightness of the assembly and prevents contamination between the samples.

After transfer is completed, the membranes can be removed, separated and dried. The separated membranes are placed into individual incubation trays, for instance, where subsequent procedures, such as, detection procedures (e.g., primary antibody incubation, secondary antibody incubation, detection of the signal) are performed. To ensure that the membrane does not fold during incubation a membrane holder, for instance which fixes the upper surface of the membrane to the bottom of the incubation tray, may be used.

Reagents

Kit as provided herein may optionally include a transfer buffer such as TBS, KCl, or PBS to which 0.1% SDS is added.

Primary detection molecules, for instance antibodies to particular groups of proteins (e.g., proteins within a specific biochemical pathway) optionally may be included with a kit. In some embodiments, the user supplies the primary detection molecule(s) (such as primary antibodies, nucleic acids probes for hybridization, and so forth).

In lieu of antibodies, other ligands may be employed as detectors. Ligands can be antibody fragments, receptors, receptor ligands, enzymes, viruses or viral particles, enzyme substrates or other small molecules that bind to specific proteins, as well as nucleic acids that bind to protein or nucleic acids. Moreover, in addition to identifying proteins of interest structurally, kits can also be employed to identify the functional state of proteins. One way to do so is to use protein modification-specific binding agents, such as phospho-specific antibodies to determine the phosphorylative state of protein(s) of interest.

Another approach to identifying protein function is to first renature the proteins on the membranes by any of a number of techniques known in the art, for instance incubating the membrane in Triton-X® (octylphenol polymerized with ethylene oxide). Once renatured, proteins will regain their enzymatic activity and one of several substrate degradation assays known in the art can be used. With this approach the activity of classes of proteins, for instance, kinases, phosphates and metalloproteinases, can be determined on the membranes using known techniques.

It will also be appreciated that the methods and devices described allow not only the simultaneous characterization of a large number of different biomolecules (e.g., proteins) but also permits characterization of a large number of characteristics of a single molecule, such as a protein, based on number of different characteristics. For example, the protein p70 S6 kinase, required for cell growth and cell cycle progression, is activated by phosphate group attachments (phosphorylation) to threonine on position 229 and/or 389 of the protein. Identification of this kinase using methods described herein could involve not only determination of its presence or absence, or quantity, but also determination of its activity. Using a stack of for membranes, for instance, one can make four copies of the biomolecular content of the plate. The first membrane could be incubated in antibody specific for the whole target protein (in this case, p70 S6 kinase), to determine whether this enzyme is present in each sample. The second membrane can be used in a kinase activity assay, to determine if the enzyme is active or not. The third membrane can be probed with phospho-p70 S6 kinase (Thr229) antibody (specific to a phosphorylated species of the protein), to determine if activity of the enzyme is due to activation at this site. The fourth membrane can be probed with phospho-p70 S6 Kinase (Thr389) antibody (specific to a different phosphorylated species of the protein), to determine if the activity of the enzyme is due to activation of that site. Since the methods described herein permit all of these tests to be done on a single set of samples from a single application to the wells of a multi-well plate (rather than on different preparations of the same samples), the information obtained is more reliable and consistent.

Panels of samples or detectors, for scientific research for instance, may be grouped by the proteins involved in a particular cellular phenomenon such as apoptosis, cell cycle, signal transduction, etc. Panels for clinical diagnostics may be grouped by proteins associated with a particular disease such as Alzheimer's disease, prostate cancer, etc.

Image Analysis Software

Software may also be provided for use with methods, devices or kits described herein, for instance to analyze and/or overlay the images of spots (features) produced on the membranes after transfer. The software is adapted to quantify the biomolecules (e.g., proteins or nucleic acids) by determining the density of the spot/feature (for instance, based on the intensity of signal from a label) and comparing these densities to a control. This process is known as "normalization." A variety of commercially available programs may be employed, such as, the 1D Image Analysis Software available from Eastman Kodak Co. or Image Quant Software available from Amersham Biosciences. The software preferably allows the user to select the kind of comparative analysis to be performed (for instance, comparing the spots present in one sample with those in another sample, or comparing the spots present on one membrane with those of another membrane within the same membrane stack). Results of the analysis is displayed in tabular format and user is given the option to go back and compare magnified sections of the images of interest.

Use and Applications

The methods, devices and kits provided herein may be used, for example, to rapidly determine the effect of a large number of therapeutic compounds on molecular profiles of living cells. By way of example, approximately 10,000 living cells are placed and cultured either in the wells 26 upper plate 20 or in a separate multi-well device (such as a standard 96-well plate) and later transferred to plate 20. Each cell group (sample) can be incubated with a separate (or combination of) candidate therapeutic compounds. The dose range and time of incubation can be varied depending on the goals of the evaluation.

After the incubation is complete, some or all of the cells are lysed (for instance, in a buffer), the lysate is optionally cleared, and some or all of the lysate is transferred to upper plate 20 if not already there. (Cells exposed/treated/incubated in a separate device may be optionally spun down with a centrifuge with the supernatant removed to remove unsolubilized debris.)

In lysed cell samples, if the concentration of protein in a sample is more than 1.0 µg/µl, it may be advisable to remove DNA from the lysed sample so that the genomic DNA does not clog pores of the membranes.

After the transfer of sample to a membrane stack, the membranes 16 are separated from stack 14. Each can then be incubated in a separate solution of detector molecule, such as a primary antibody (or nucleic acid probe) specific for a desired target. After incubation, for instance for about 1-8 hours, the membranes are washed in buffer to remove unbound detection molecules.

For detection of the spots (features), where the samples contain proteins and the primary detector molecule is an antibody, the membranes are incubated in a secondary antibody that binds to the primary antibody. By way of example, the secondary antibody is covalently linked to an enzyme such as horseradish peroxidase (HRP) or alkaline phosphatase (AP), which catalyzes a detectable reaction in the presence of the appropriate substrate. Thus, the protein/antibody complex can be visualized using a number of techniques such as ECL, direct fluorescence, or colorimetric reactions. ECL is preferred in some embodiments. Commercially available flatbed scanners may be employed in conjunction with photographic film to detect many signals, including ECL. Alternatively, specialized imaging instrumentation for ECL, such as the IMAGE STATION available from Eastman Kodak, may be utilized. Digital imaging software can be employed to display the images according to the preference of the user.

Similar techniques can be used to detect the presence of nucleic acids in spots on the membranes, by hybridizing a detectable probe nucleic acid to the membrane(s) and detecting the binding of the probe. Hybridization techniques and appropriate conditions for carrying them out are well known in the art.

Alternatively, described methods, devices and kits may be employed to detect total proteins as well as specific proteins simultaneously on each membrane. This allows a user to normalize the signal from the specific protein(s) based on the amount of total protein loaded. For this purpose, membranes—after transfer—can be incubated in the EZ-Link Sulfo-Biotin-NHS solution (Pierce, Cat. No. 21217), which is known for it's high affinity to bind to virtually all proteins. After the membranes are biotinylated, primary antibody incubation is carried out. Fluorescence-based detection is then employed. Applying a mixture of streptavidin (or avidin)-linked Fluorophore 1 and secondary antibody-linked Fluorophore 2, the user can achieve simultaneous detection of total (by Fluorophore 1) and specific (by Fluorophore 2) proteins on the same membrane by scanning the membrane on a fluorescent scanner. Example scanners include Storm or Typhoon available from Amersham Biosciences (Piscataway, N.J.) (Cat. No. 63-0055-79).

The highly parallel analyses methods provided herein may be used to identify proteins in any biological sample, including but not limited to bodily fluids (e.g., blood, plasma, serum, urine, bile, cerebrospinal fluid, aqueous or vitreous humor, or any bodily secretion), transudates, exudates (e.g. fluid obtained from an abscess or any other site of infection or inflammation), or fluid obtained from a joint. Additionally, a biological sample can be obtained from any organ or tissue (including or autopsy specimen). Biological samples may comprise cells, which in some instances will be lysed or otherwise permeabilized prior to being transferred to/through a stack of membranes.

Described methods, devices and kits may also be employed to provide a proteomic profile of cells from tumors that have been exposed to various pharmacological agents (and combinations thereof), such as those known to impact signaling pathways. The results of such analyses will help clinicians select the optimum drug or cocktail of drugs to treat the particular tumor.

It will be appreciated that because the size of the membrane array can be varied, the user has the option of analyzing a large number of different samples in parallel, thereby permitting direct comparison between different patient or other samples. For example, different samples from the same patient at different stages of disease can be compared in a side-by-side arrangement, as can samples from different patients with the same disease.

While the following examples illustrate the detection of proteins, nucleic acids and other biomolecules can also be detected using the provided methods, devices and kits.

EXAMPLE 1

Transfer from Multi-Well Plate to Membranes

This example demonstrates that protein, i.e., BSA, contained in liquid samples can be transferred from a multi-well sample holder to a plurality of stacked membranes. The example further demonstrates the low variability between two adjacent samples containing the same amount of protein on the same membrane. In addition, the example demonstrates the low variability between membranes with respect to the amount of protein in a single sample that is transferred to the multiple membranes.

A Hybri-Slot 24-Well Filtration Manifold apparatus from Invitrogen (Carlsbad, Calif.) was used in this example. Ten membranes were sized to 12 cm×3 cm and soaked in ddH$_2$O for 2 minutes. The ten membranes were then placed between the top and bottom plate of the vacuum manifold. The apparatus was assembled in accordance with the manufacturer's recommendations.

Twelve microfuge tubes were filled with extraction buffer (3 M KCl, 10 mM TRIS pH 7.5, 100 mM NaCl, 50 mM EDTA; 1:100 dilution of phosphatase-inhibitor cocktails I and II (Sigma)) containing increasing amounts of bovine serum albumin (Sigma) as indicated in TABLE 1. The final volume in all of the tubes was 200 µl.

TABLE 1

| TUBE # | 1 | 2 | 3 | 4 | 5 | 6 | 7 | 8 | 9 | 10 | 11 | 12 |
|---|---|---|---|---|---|---|---|---|---|---|---|---|
| BSA conc (µg/µl) | 0 | 0.002 | 0.01 | 0.02 | 0.04 | 0.08 | 0.12 | 0.16 | 0.2 | 0.24 | 0.28 | 0.32 |

The contents of each tube were mixed and 50 µl of each sample was placed in a separate well in the first row of the multi-well sample holder component of the vacuum apparatus as indicated in TABLE 2. Samples were loaded in the identical fashion into the second row of the multi-well sample holder.

TABLE 2

| Well # | 1 | 2 | 3 | 4 | 5 | 6 | 7 | 8 | 9 | 10 | 11 | 12 |
|---|---|---|---|---|---|---|---|---|---|---|---|---|
| Sample vol (µl) | 50 | 50 | 50 | 50 | 50 | 50 | 50 | 50 | 50 | 50 | 50 | 50 |
| BSA conc. (µg/µl) | 0 | 0.002 | 0.01 | 0.02 | 0.04 | 0.08 | 0.12 | 0.16 | 0.2 | 0.24 | 0.28 | 0.32 |
| BSA amount (µg) | 0 | 0.1 | 0.5 | 1 | 2 | 4 | 6 | 8 | 10 | 12 | 14 | 16 |

After the wells of rows 1 and 2 of the apparatus were loaded with sample, vacuum was applied to the apparatus and filtration was allowed to proceed for 20-30 minutes, under the conditions recommended by the manufacturer. During that time period the entire sample volume in each well passed through the membrane stack. The membrane stack was removed from the apparatus and the membranes were rinsed and separated in TBST buffer (150 mM NaCl, 50 mM TRIS pH 8.0, 0.05% Tween-20). Membranes were dried individually at room temperature on Chromatography paper 3 mm Chr filter paper (Whatman) and then stained to detect total protein using Sypro Ruby Staining solution (Molecular Probes) according to manufacturer's recommendations.

Figure 3:
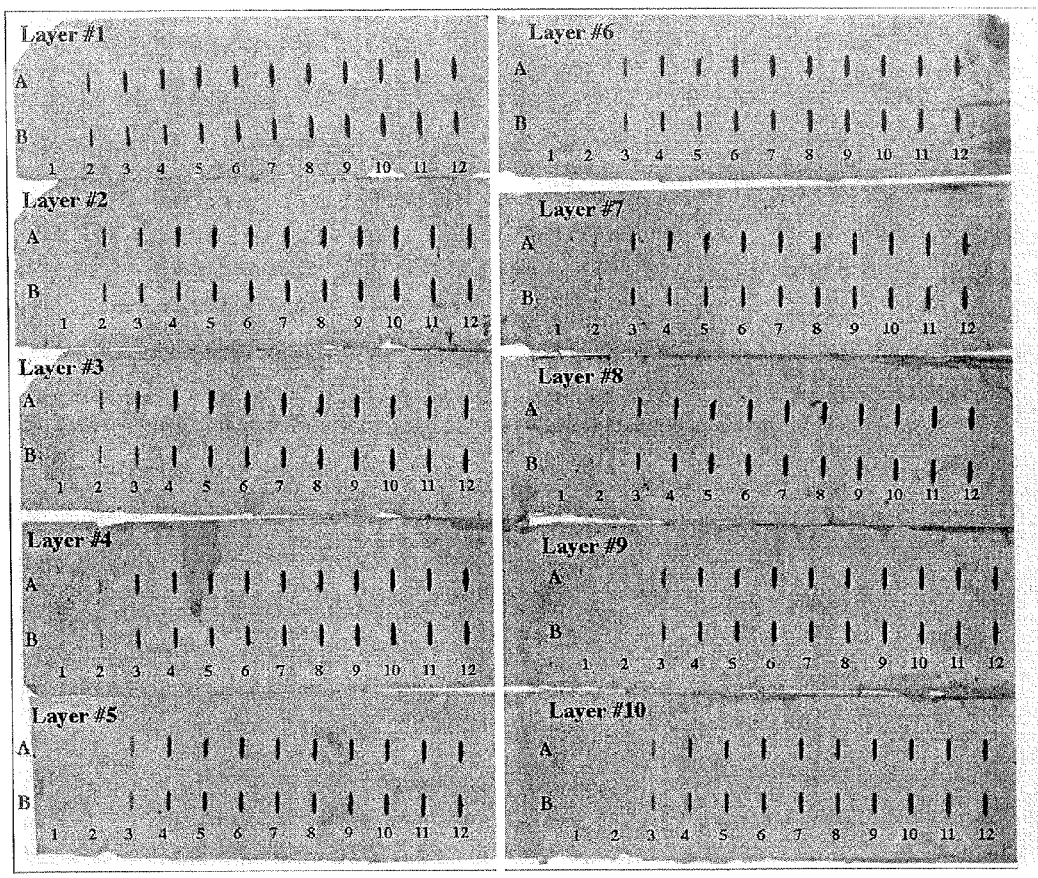
FIG. 3 shows a series of ten membranes to which varying amounts of BSA was transferred, as described more fully in the Examples. The membranes were stained with a total protein stain (i.e., Sypro Ruby stain from Molecular Probes), to visualize the transferred BSA.

FIG. 3 shows the stained membranes. All of the stained membranes were scanned at the same time in Storm Scanner (Amersham). The resultant image was stored in TIFF format and imported into Kodak 1D Analysis program (Kodak) where band intensities were determined Data were sorted and analyzed in Excel (Microsoft). Data from three independent experiments were analyzed.

Variability between two adjacent samples having the same protein concentration on the same membrane was ≤3% regardless of the position of the membrane in the stack. In addition, where 2.0 µg or more of protein was loaded into a sample well, the variability among membranes of a 10-membrane stack was 20-30% for any particular sample. These data support the finding that stacks of membranes, as disclosed herein, can be used in a vacuum manifold to generate membrane replicas of the liquid sample.

EXAMPLE 2

Detection of Specific Proteins

This example demonstrates that specific proteins could be detected by antibodies incubated with replicate membranes made by the method described in Example 1.

Human epithelial cell line A431 (vulvar squamous carcinoma origin) was maintained at 37° C. and 5% $CO_2$ in Dulbecco's modified Eagle's medium (DMEM) supplemented with 10% fetal bovine serum (FBS) and antibiotics (Life Technologies, Inc.). To analyze signal transduction in the absence of growth factors, cells were grown to 50-60% confluency in 6-well culture plates (#3046, Falcon, Lincoln Park N.J.). Once a desired cell density was reached, the cells were washed twice in sterile Dulbecco's phosphate-buffered saline (DPBS) and incubated for 24 hours in DMEM containing 0.1% FBS, in order to induce quiescence.

Quiescent cells were incubated for 2 hours with various concentrations of the PI3 kinase inhibitor LY294002 (2-(4-morpholinyl)-8-phenyl-chromone; Cell Signaling) ranging from between 2 to 50 µM. Complete inhibition of Akt kinase activity was achieved at concentrations of LY294002 between 10 to 50 µM, while only partial inhibition was achieved with lesser concentrations (e.g., 2 and 5 µM).

Following incubation with the inhibitor, the treated cells were washed twice in cold DPBS and extraction buffer (3M KCl, 10 mM TRIS pH 7.5, 100 mM NaCl, 50 mM EDTA; 1:100 dilution of phosphatase-inhibitor cocktails I and II (Sigma)) was added to achieve a density of $1\times10^5$ cells/ml. The cells were scraped off the tissue culture plates, transferred into microfuge tubes and vortexed for 3 minutes. After 30 minutes incubation at room temperature with occasional vortexing, the tubes were centrifuged at 14,000 RPM for 4 minutes and the supernatants were separated into fresh tubes. The total protein concentration of each supernatant was determined using the BCA Protein Assay (Pierce).

A ten-membrane stack was briefly wetted in distilled water and "sandwiched" between upper and the lower manifold plates as described in Example 1. All the wells of the manifold were filled with 100 µl of the supernatants to be tested. The vacuum was applied to the apparatus until the wells ran dry, which took approximately 10-30 minutes. The manifold was disassembled and the individual membranes were separated and dried briefly.

One of the membranes was incubated in 1:200 dilution of anti-phospho-Akt (S473) (Pharmigen) in TBST with 0.5% BSA at 4° C. for 8-12 hours. The membrane was washed 3 times for 5 minutes each in TBST and incubated in a 1:2,000 dilution of anti-rabbit secondary antibody (Amersham) for 30 minutes at room temperature. Following incubation with the secondary antibody, the membrane was washed 3 times for 5 minutes each in TBST. Phospho-Akt transferred to the membrane was visualized using ECL Plus Reagent (Amersham) and BioMax film (Kodak).

Figure 4:
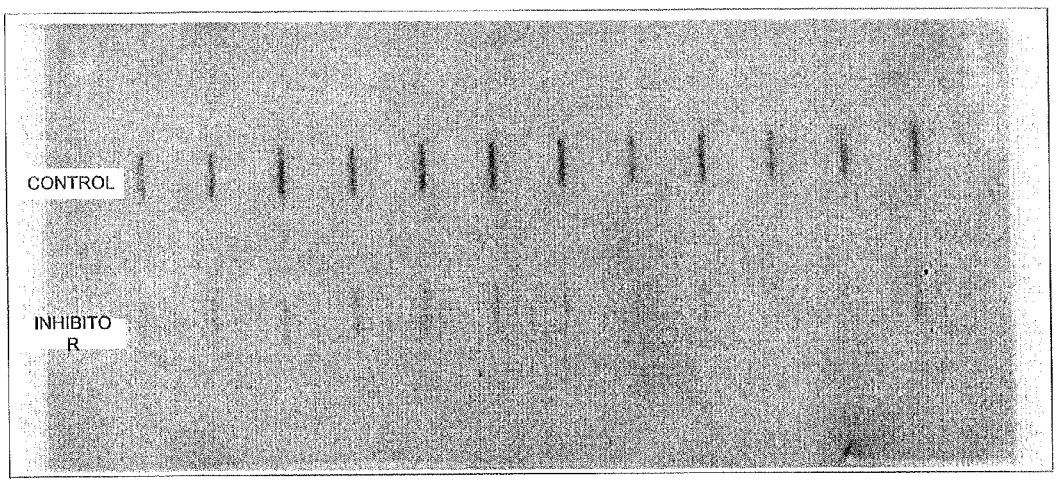
FIG. 4 is an image of a Western blot of a cellular extract made from human epithelial cell line A431 treated with PI3 kinase inhibitor LY294002 (row marked "INHIBITOR") and control A431 cells which were untreated (row marked "CONTROL"). Clarified total cell extracts were transferred to a stack of ten membranes according to a method described herein. The membrane shown was then probed with an antibody specific for the phosphorylated form of the Akt protein.

As shown in FIG. 4, protein extracted from cells incubated with LY294002 ("INHIBITOR" in FIG. 4) contained little, if any, detectable phospho-Akt. In comparison, extracts of cells that were not exposed to the kinase inhibitor ("CONTROL" in FIG. 4) show the presence of phospho-Akt.

These results demonstrate that a functional (i.e., phosphorylated) form of the Akt protein was detectable on membranes prepared as described in Example 1, and that there was a clear difference between the extracts of cells treated with LY294002 kinase inhibitor and untreated, control cells.

EXAMPLE 3

Simultaneous Detection of Total and Specific Proteins

This Example illustrates the simultaneous detection of total protein and specific proteins in a single sample transferred to multiple membranes, as described in Example 1.

Primary lymphocytes were treated with different chemical compounds that affect cell metabolism in a variety of ways. After extracting proteins from the cells as described in Example 2, samples were transferred through a 5-membrane stack using a Bio-Dot Microfiltration System (Bio-Rad, Cat. No. 170-6545) as described in Examples 1 and 2.

After transfer was completed, the membranes were separated, washed, air dried, and incubated in EZ-Link Sulfo-Biotin-NHS solution (Pierce) to nonspecifically biotinylate all proteins captured on the membrane. Then, each membrane was incubated in a different primary antibody solution (pTyr, pAKT, pRB, PCNA, pERK, as indicated in FIG. 6) under the conditions described in Example 2.

Following incubation with the primary antibodies, a mixture of FITC-labeled streptavidin (streptavidin-fluorphore 1, Molecular Probes, Cat. No. S-869) and Cy 5-labeled secondary antibody (secondary antibody-fluorphore 2, Amersham Biosciences, Cat. No. PA 45004) was applied to the membranes. After incubation, the membranes were washed, dried and scanned on Typhoon Scanner (Fluorescent Scanner, Amersham Biosciences, Cat. No. 63-0055-79) using different wavelengths to detect the different fluorophores.

Figure 6:
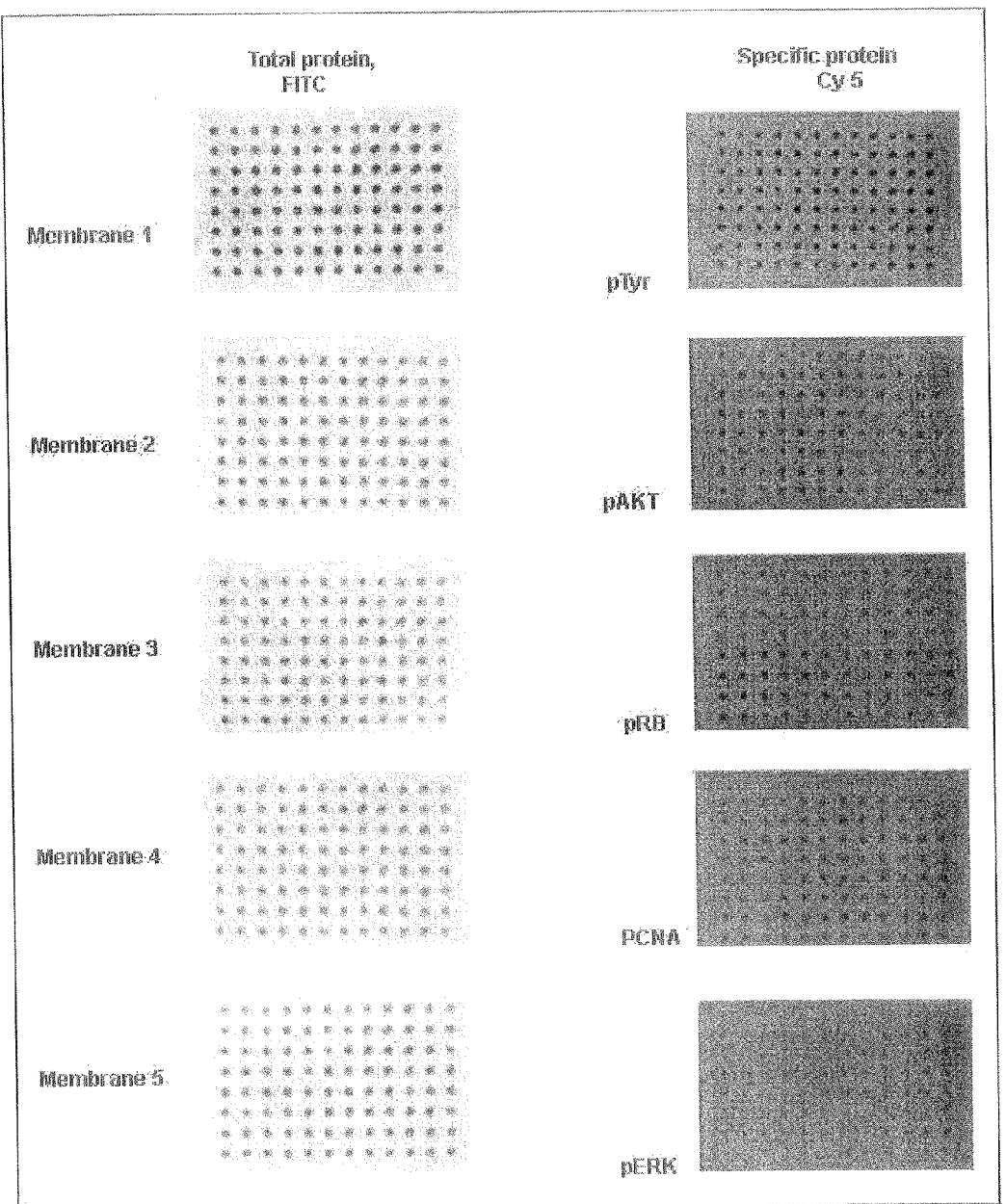
FIG. 6 shows images of five membranes, each stained with a total protein detector and a specific protein detector, i.e., an antibody specific for Cy5.
Figure 7:
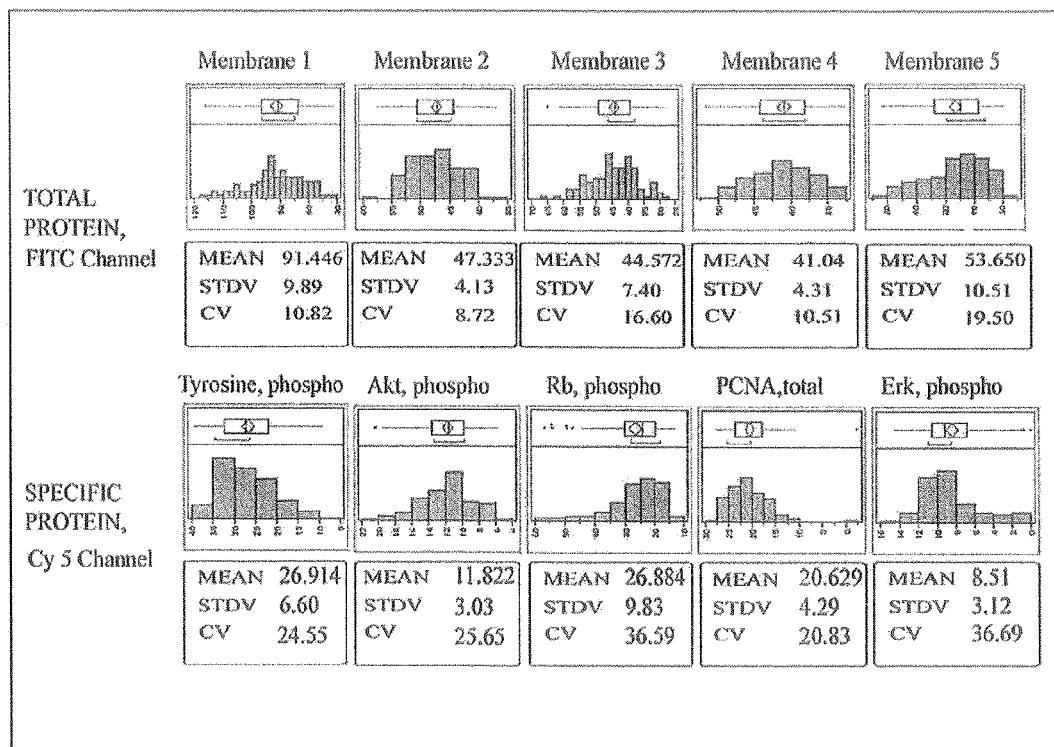
FIG. 7 shows quantitative analysis of the protein amounts shown in FIG. 6.

As shown in FIGS. 6 and 7, a uniform signal was measured on the channel used to detect FITC-labeled streptavidin, which binds the non-specifically biotinylated proteins. On the other hand, the signal arising from the Cy 5-labeled secondary antibody, which binds to each of the primary antibodies, was consistent with differential expression of the specific proteins recognized by those primary antibodies.

The scanned images shown in FIG. 6 were analyzed using "Image Quant" Software (Amersham Biosciences, Cat. No. 63-00-4626), JMP Statistical Analysis Program (SAS Institute, Inc.), and Principal Component Analysis (Paytek Pro) to produce the graphs shown in FIG. 7. A numerical value for intensity of each dot on every membrane was obtained. The signals from specific proteins were normalized for the total protein loading and the resulting data was analyzed using JMP software (v.3.1, NCI). Statistical analyses show that the standard deviation and variability coefficient values for total proteins are much less than for specific proteins, which means that different proteins in the samples were expressed differentially, while total proteins were similarly loaded.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims.

We claim:

1. Apparatus for detecting biomolecules from a biological sample, comprising: at least one porous polycarbonate membrane coated with nitrocellulose on one or both sides, said nitrocellulose having an affinity to one or more biomolecules from said sample; wherein the nitrocellulose coated polycarbonate membrane is track-etched, less than about 30 microns thick and has a pore size ranging from between about 0.1 to 5.0 microns, and wherein said membrane is further characterized as possessing a high affinity for biomolecules, but has a low capacity for retaining such molecules.

2. The apparatus of claim 1, wherein the polycarbonate membrane is between 4-20 microns thick and has a pore size of about 0.4 microns.

3. The apparatus of claim 1, comprising at least 5 coated polycarbonate membranes.

4. The apparatus of claim 3, wherein each polycarbonate membrane is less than about 30 microns thick and has a pore size ranging from between about 0.1 to 5.0 microns.

5. The apparatus of claim 3, wherein each polycarbonate membrane is between 4-20 microns thick and has a pore size of about 0.4 microns.

6. The apparatus of claim 3, wherein the polycarbonate membranes are separable.

* * * * *